US008386192B2

(12) United States Patent
Kawasaki et al.

(10) Patent No.: US 8,386,192 B2

(45) Date of Patent: Feb. 26, 2013

(54) DISEASE DIAGNOSIS SUPPORT SYSTEM

(75) Inventors: Shingo Kawasaki, Tokyo (JP); Noriyoshi Ichikawa, Tokyo (JP); Fumio Kawaguchi, Tokyo (JP); Hideo Kawaguchi, Saitama (JP); Naoki Tanaka, Saitama (JP); Masahiko Mikuni, Maebashi (JP); Masato Fukuda, Maebashi (JP)

(73) Assignees: Hitachi Medical Corporation, Tokyo (JP); Hitachi, Ltd., Tokyo (JP); National UniversityCorporation Gumna University, Gunman (JP)

( * ) Notice: Subject to any disclaimer, the term of this patent is extended or adjusted under 35 U.S.C. 154(b) by 1480 days.

(21) Appl. No.: 11/916,892

(22) PCT Filed: Jun. 8, 2006

(86) PCT No.: PCT/JP2006/311507

§ 371 (c)(1),
(2), (4) Date: Dec. 7, 2007

(87) PCT Pub. No.: WO2006/132313

PCT Pub. Date: Dec. 14, 2006

(65) Prior Publication Data

US 2009/0118602 A1 May 7, 2009

(30) Foreign Application Priority Data

Jun. 9, 2005 (JP) ................................ 2005-169633

(51) Int. Cl.
*G01N 33/48* (2006.01)

(52) U.S. Cl. ........................................................ 702/23

(58) Field of Classification Search ..................... 702/23
See application file for complete search history.

(56) References Cited

U.S. PATENT DOCUMENTS

| | | | | |
|---|---|---|---|---|
| 5,746,204 | A | 5/1998 | Schauss | |
| 2005/0177033 | A1* | 8/2005 | Kawasaki | 600/315 |
| 2007/0055118 | A1* | 3/2007 | Kawasaki et al. | 600/323 |

FOREIGN PATENT DOCUMENTS

| | | |
|---|---|---|
| EP | 1 506 739 | 2/2005 |
| EP | 1 665 985 | 6/2006 |

OTHER PUBLICATIONS

Suto et al, "Multichannel near-infrared spectroscopy in depression and schizophrenia: cognitive brain activation study", Biological Psychiatry, vol. 55, No. 5, Mar. 1, 2004, pp. 501-511.

Matsuo et al, "Alteration of Hemoglobin Oxygenation in the Frontal Region in Elderly Depressed Patients as Measured by Near-infrared Spectroscopy"; J. Neuropsychiatry Clin Neurosci, vol. 12, Nov. 1, 2000, pp. 465-471.

* cited by examiner

*Primary Examiner* — Jerry Lin

(74) *Attorney, Agent, or Firm* — Antonelli, Terry, Stout & Kraus, LLP.

(57) ABSTRACT

There is provided a system for supporting the assessment as to which disease group the subject to be examined falls in or what position in the whole disease group the subject is in. This support system comprises the data storage part which stores feature values of optical bio-measurement data of many subjects including patients in multiple disease groups, the analysis part which extracts plural kinds of feature values from the optical bio-measurement data and the display part which displays the results of analysis in the analysis part associated with the dictionary data, wherein the display part produces a scatter diagram on which features values of the dictionary data are plotted, with one of the two feature values being plotted along the axis of abscissa and the other along the axis of ordinate, and displays the positions of the subject to be assessed on the scatter diagram superimposed on the scatter diagram. With this scatter diagram, the relationship between the features of the subject and the feature of the disease group can be known in one glance.

15 Claims, 8 Drawing Sheets

DISEASE DIAGNOSIS SUPPORT SYSTEM

FIELD OF THE INVENTION

The present invention relates to the system for supporting the assessment (diagnosis) of various diseases using results of measurement with a biological photometric device, and particularly to the effective system for the diagnosis of psychiatric disorders such as schizophrenia, bipolar disorder and depression.

PRIOR ART

The biological photometric device is an apparatus to irradiate near infrared light on the living body and measure the light which passes through the living body or reflects inside the living body. In view of its capability of measuring changes in blood circulation, hemodynamics and the hemoglobin amount easily, simply and with less constraint and damage to the subject, the clinical application of the biological photometric device is strongly expected.

It has been reported that the biological photometric device has been applied to the applications such as diagnosis of epilepsy, cerebral ischemia and others and research on linguistic function. Non-patent documents 1 and 2 below report that the optical bio-measurement shows abnormality in the changing pattern of the hemoglobin amount in the frontal lobe of the patients suffering from psychiatric disorders such as depression and schizophrenia. Specifically, it has been reported that the comparison of the integration values of hemoglobin time-domain waveforms when the task was given between healthy persons, depression patients and schizophrenia patients, revealed different characteristics as large, medium and small. It has been also reported that the level of hemoglobin re-increased after the completion of task in schizophrenia patients.

On the other hand, the applicant of the present patent proposes a biological photometric device which is equipped with the functions to extract features from the changing patterns of the hemoglobin amount, and numerize and display them by disease (Patent Document 1). The applicant further proposes an apparatus which supports the diagnosis of the subject by calculating the similarity between the feature value data of the patient group whose diagnosis has been finalized and the feature value data of the subject (Patent Document 2). This apparatus provides and displays the probability that the subject is of any particular disease by using the length of Mahalanobis distance from particular disease as a measure indicating the similarity.

Non-Patent Document 1

"Dynamics of local cerebral blood flow in the frontal lobe in psychoneurotic disorders—Study using optical topography" Masato Fukuda, The report of the study supported by the grant from Japan Society for the Promotion of Science in 2001-2002.

Non Patent Document 2

"Hikari de miru kokoro", Masato Fukuda, "Kokoro to Shakai" vol. 31, Issue 1 Supplementary Volume, Japanese Association of Mental Health.

Patent Document 1

Japan Published unexamined patents application No. 2003-275191

Patent Document 2

WO No. 2005/025421

DISCLOSURE OF THE INVENTION

Problem to be Solved by the Invention

However, since the technology described in Patent Document 2 calculates the center of gravity the feature value for the disease group to be used as a basis of the assessment and its distance from the feature value of the subject, it was difficult to identify the trend of the feature value which demarcates each disease group (including healthy group). It was also difficult to identify where the subject is located in the whole picture of all diseases.

Accordingly, the object of the present invention is to provide a disease diagnosis support system which can easily identify the correlation between each disease group and the feature value and the location of the subject in all diseases, and can support to achieve more accurate diagnosis.

Means for Solving the Problems

In order to solve the aforementioned problems, the disease diagnosis support system of the present invention comprises an analysis part for extracting plural kinds of feature values from hemoglobin signals obtained by optical bio-measurement and a display part displaying the results of analysis performed in the analysis part, wherein the display part produces a scatter diagram for at least one of the plural kinds of feature values, and displays the feature values plotted on the scatter diagram.

The disease diagnosis support system of the present invention is further equipped with a data storage part for storing the feature values of optical bio-measurement data of a large number of subjects including the multiple number of disease groups as dictionary data, wherein the display part displays the analysis results obtained at the analysis part in relation to the dictionary data. The display part produces a scatter diagram for two feature values among plural kinds of feature values, on which one of these values of the dictionary data are plotted along the axis of abscissa and the other values along the axis of ordinate, and displays the two feature values extracted for the subject to be assessed as superimposed on the scatter diagram.

The disease diagnosis support system of the present invention is preferably equipped with a classification part, which classifies the dictionary data stored in the storage part into several different patterns by using the plural kinds of feature values, and the display part displays the types classified by the classification part as superimposed on the scatter diagram.

In the disease diagnosis support system of the invention, the classification part classifies, for example, the dictionary data by combining threshold values of plural kinds of feature values, wherein the classification is performed by using the combination of threshold values which minimizes the entropy of the distribution of disease groups in the classified types.

In the disease diagnosis support system of the present invention, the display part displays, for example the number of disease groups contain in each types classified by the classification part, together with the scatter diagram. When the data stored in the storage part are updated, the classification part also updates the classification results and displays them in the display part.

Further, the disease diagnosis support system of the present invention comprises a memory part provided in the analysis part, which stores analytical results of data measured for the same subject at different times and displays temporal changes in the analytical data on the display part.

In the disease diagnosis support system of the present invention, the disease groups include, for example, schizophrenia, bipolar disorder and depression. The plural kinds of feature values include the integration values and gradients of the specified part of the optical bio-measurement waveform.

The diagnosis support method of the present invention is a diagnosis support method for providing information necessary for diagnosing the disease of the subject by using hemoglobin signals measured by the optical bio-measurement, and comprises the steps of extracting one or more feature values from each hemoglobin signals of persons to whom definitive diagnosis has been made to produce dictionary data, extracting one or more feature values from the hemoglobin signal of a subject to be examined, producing a scatter diagram of the one or more feature values, and displaying the feature values extracted for the subject, together with the feature values constituting the dictionary data on the scatter diagram.

Effect of the Invention

According to the present invention, by the superimposition display of the feature values of the subject to examined on the scatter diagram of pre-registered disease dictionary data, it becomes possible to identify instantly in which disease group the subject is likely to be classified and where the subject is positioned in the whole disease group. Particularly, by displaying the area which demarcates the types resulting from the classification on the scatter diagram, said identification can be performed easily.

Further, according to the present invention, by adding temporal processing function, not only the data at one time point, but also temporal changes of the data of the subject can be observed. This allows the confirmation of treatment effect, supports the decision making regarding the clinical policy, and provides a very useful system not only for the assessment but also for the treatment of psychiatric disorders.

BEST MODE FOR CARRYING OUT THE INVENTION

Embodiments of the present invention will be explained below with the reference of the attached drawings.

Figure 1:
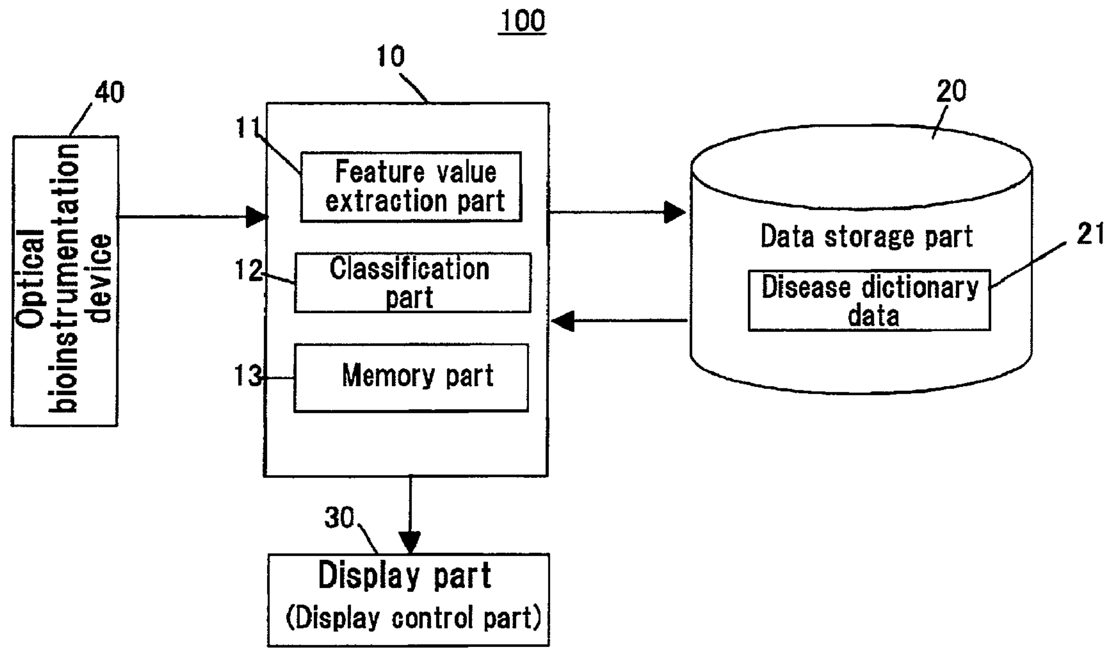
FIG. 1 A block diagram showing one embodiment of the disease diagnosis support system of the present invention FIG. 2 A block diagram showing one embodiment of the biological photometric device in the disease diagnosis support system of the present invention FIG. 3 A diagram showing hemoglobin change waveforms measured by the biological photometric device FIG. 4 A diagram showing characteristic waveforms by disease FIG. 5 A flow diagram showing actions of the biological photometric device of the present invention FIG. 6 A diagram showing an example of a scatter diagram displayed by the disease diagnosis support system of the present invention FIG. 7 A diagram showing disease assessment algorithm FIG. 8 A diagram showing an example of disease group distribution chart displayed together with the scatter diagram shown in FIG. 6.

FIG. 1 is a block diagram showing the outline of the disease diagnosis support system 100 of the present invention. This disease diagnosis support system 100 comprises the analyzing part 10 which performs various signal processing and analysis procedures to the hemoglobin change signals measured in the biological photometric device 40, the data storage part 20 which stores the results of analysis of optical bio-measurement data obtained from a number of objects as disease dictionary data, and the display part 30 which displays the results of analysis by the analysis part 10.

Figure 2:
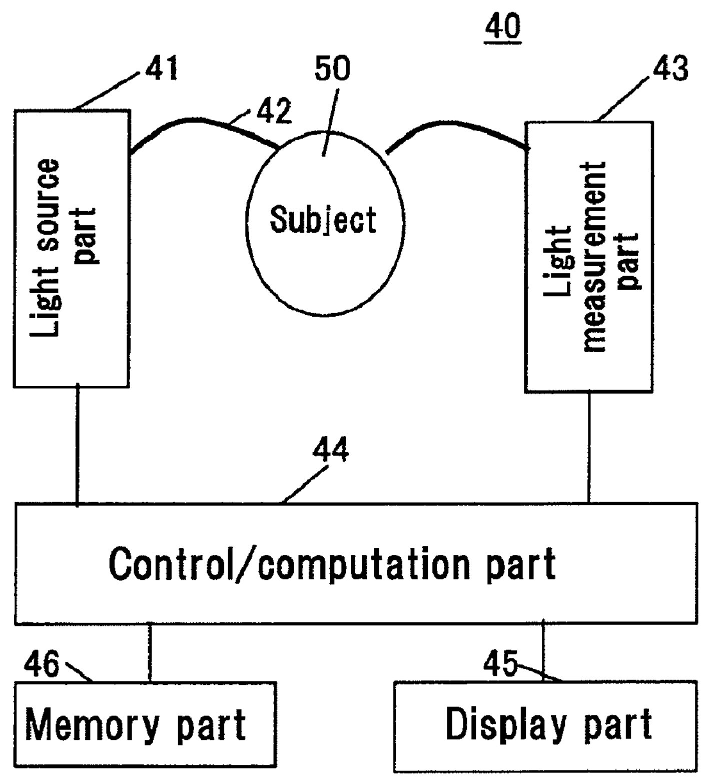

The biological photometric device 40 is an apparatus to irradiate the light on the human head, receives the light which are reflected from or scattered at the vicinity of the surface of the head, and measures change signals of intra-blood substance (hemoglobin in this case) and a multi-channel measurement apparatus for measuring signals from multiple positions. The specific structure of the apparatus comprises, as shown in FIG. 2, the light source part 41, the light measurement part 43, the control/computation part 44, the display part 45, the memory part 46 and others.

The light source part 41 generates the light with a predetermined wavelength given different modulation depending on the position of measurement, and irradiates it on the head of the subject 50 through the multiple number (omitted in the Figure) of the optical fibers 42. The light reflected and scattered in the vicinity of the head part is transmitted to the optical measurement part 43 through the light receiving optical fiber located in the vicinity of the transmitting optical fiber, where it is converted to the intensity of light at every measurement point. Optical measurement is performed by giving predetermined task such as linguistic stimulation and finger tapping to the subject, and the difference in the conditions under task and without task is obtained as hemoglobin change signals. The hemoglobin change signals are usually measured for both oxygenated hemoglobin and deoxygenated hemoglobin, and either or the total of both hemoglobin change signals are used depending on the disease to be assessed.

Figure 3:
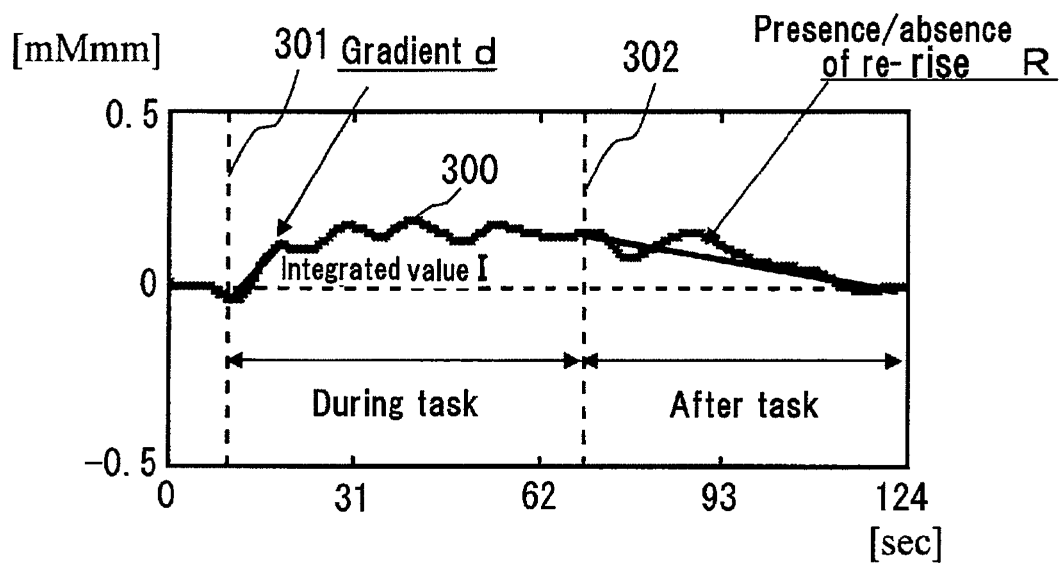

The hemoglobin change signals are obtained, as shown in FIG. 3, for example, as the waveform 300 showing changes (mMmm) in signal intensity at given times in the period before, during and after the provision of the task. Two vertical lines shown in FIG. 3 represent the task starting point 301 and the task completion point 302, respectively. The task, with the combination of its loading and suspending as one set, is repeated for several times. Hemoglobin waveforms obtained by several measurements are averaged and subjected to preprocessing such as smoothing and baseline processing where appropriate. FIG. 3 shows a hemoglobin change waveform, and in case the biological photometric device 40 is a multiple channel device, said waveform is obtained for each channel.

The control/computation part 44 controls the actions of the light source part 41 and the light measurement part 43, as well as performs necessary processing for displaying hemoglobin change signals from the light measurement part 43 on the display part 45. The memory part 46 memorizes the measured hemoglobin change signals and necessary data for processing of the control/computation part 44.

The analysis part 10 comprises the feature value extraction part 11, which inputs hemoglobin change signals produced by the biological photometric device 40 and extracts the feature values, the classification part 12, which classifies a large number of feature values into multiple number of types, the memory part 13, which memorize the feature values of the subject extracted by the feature value extraction part 11, and others. The analysis part 10, though it is not shown in the figure, is equipped with the input device which sends commands to each part, and input data and parameters which are necessary for the action of each part. The function of each component of the analysis part 10 will be described later.

The data storage part 20 stores the feature value data 21, which consists of plural kinds of feature values extracted from optical bio-measurement data of the subjects such as psychiatric patients and healthy subjects, as disease dictionary data. The feature values in this disease dictionary data are of the same kinds with those extracted by the feature value extraction part 11, and are those extracted and produced by the feature value extraction part 11 of the present system or a similar feature value extraction part of the biological photometric device 40 if the device 40 is equipped with the similar feature value extraction part. The number of persons (subjects) constituting the disease dictionary data 21 is not particularly limited, but a number sufficient to be capable of statistical processing. The disease dictionary data 21 can be updated by deletion of data or addition of new data.

The display part 30 displays the feature values of the subject extracted by the feature value extraction part 11, the disease dictionary data 21 (feature value data) stored in the data storage part 20 and the results of classification of said data, and is equipped with the display device such as a display and the display control part (not illustrated in the figure) for controlling the display.

The aforementioned analysis part 10, the data storage part 20 and the display part 30 may be connected directly with the biological photometric device 40 via signal line, or they can be installed as an independent system from the biological photometric device 40. In the latter case, the said system is configured to be able to receive data measured by the biological photometric device 40 through the publicly known data transmission means, including radio transmission and internet. In case that the said system is directly connected with the biological photometric device 40, it is possible to equip the control/computation part 44, the memory part 46 and the display part 45 in the biological photometric device 40 in FIG. 2 with the function of the analysis part 10, the data storage part 20 and the display part 20 of the disease diagnosis support system, respectively.

The function of each section of the analysis part 10 will be explained below.

The feature value extraction part 11 extracts the features of waveform from the hemoglobin change waveforms shown in FIG. 3, and expresses them in numeric values. When the biological photometric device 40 is a multiple-channel apparatus and the waveform is obtained for each channel, it selects a waveform of the channel showing the strongest feature and performs the principal component analysis as necessary to extract features for one or selected number of hemoglobin waveforms. As the methods of pre-processing of the signals and the analysis of primary components, the method described in the WO 2005/025421 may be used.

Figure 4:
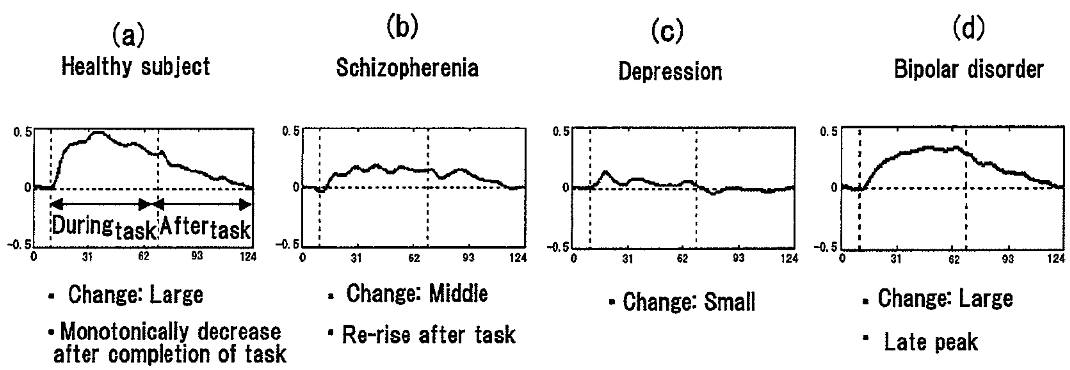

In case the disease to be measured is any psychiatric disorder such as schizophrenia, bipolar disorder and depression, the gradient d immediately after the start of task, the integrated value I of waveforms while the task is given and the re-rise R after the task is removed are used as feature values as shown in FIG. 3. FIG. 4 shows the hemoglobin change waveform (changes in the amount of oxygenated hemoglobin) by psychiatric disease. FIGS. 4(*a*)-(*d*) represent typical hemoglobin change waveforms for healthy subjects, schizophrenia, depression and bipolar disorder, respectively. As illustrated, the waveform of the healthy subjects signal values dramatically changes upon start of the task and decreases monotonically after the completion of the task, while schizophrenia is characterized by less change during the task than healthy subjects and re-rising of signal values after the completion of the task. Depression patients show less change in signal values during and after the task. In bipolar disorder patients, changes in signal values are relatively large immediately after the start of the task, but the appearance of peaks, or rise of peaks immediately after the start of the task tends, to be slow. Accordingly, there is the possibility that these disease groups are assessed by the features such as the gradient d immediately after the start of the task, the integration value I of the waveforms during the task and the presence or absence of re-rise R after the completion of the task.

The feature value extraction part 11 obtains the aforementioned features as numeric values by scanning the hemoglobin change signals along the time axis. Specifically, the gradient of the graph immediately after the start of the task is calculated from the signal value at the point when pre-determined length of time (for example, 5 seconds) elapses from the start of the task. The integrated values are calculated by sampling signal values during the task at an appropriate interval and integrating them. Re-rise is considered as "presence", if the integrated value of the waveform area, which protrudes above the linear line connecting the signals values at the end of the task and the signal values at the end of measurement, is higher than a threshold, whereas it is considered as "absence" if it is lower than the threshold.

The feature extraction by the feature value extraction part 11 is performed for the hemoglobin signals (including signals after processing, such as pre-processing and principal component analysis) of the patient, or subject, and the hemoglobin signals of the healthy subjects and the patients whose diagnosis has been confirmed by other diagnosis method. The feature values obtained for the former are stored in the memory part 13 (or data storage part 20) for displaying them in the display part 30. The feature values obtained for the latter are registered in the disease dictionary data in the data storage part 20. The feature value data registered in the disease dictionary data are classified in the classification part 12.

The classification (a clustering method) by the classification part 12 may use any publicly known method. The embodiment of the present invention employs, however, an automatic clustering method using entropy minimization. This automatic clustering is performed by finding a combination of threshold values which provides largest possible bias in presence probability of each disease group of each type, namely minimum entropy, when the disease groups with different kinds of features are classified into n types by using the combination j of the threshold values of said features.

In the example case where the disease groups of normal cases (NC), schizophrenia cases (SC), depression patients (DP) and bipolar disorder patients (BP) are classified into five types by using gradient and integration values as feature values and combining thresholds of these values, the probabilities of the presence of each patient group for each type, p NC(j,n), p SC(j,n), p DP(j,n) and p BP(j,n) satisfy the following equation.

$$pNC(j,n)+pSC(j,n)+pDP(j,n)+pBP(j,n)=1 \quad \text{[Formula 1]}$$

The sum of entropies E(j) for the combination j of threshold values is expressed with the following equation, $$E(j) = \sum_n pnE(j, n)$$

[Formula 2]

$$E(j, n) = -\sum_\alpha p\alpha(j, n)\log_2 p\alpha(j, n)$$

$$\alpha = NC, SC, DP, \text{ or } BP$$

where pn is the percentage of data contained in type n for the combination j of threshold values. The combination j of threshold values is selected so as to minimize said E(j). The classification part 12, in this way, classifies the feature value data registered in the disease dictionary data into multiple types. When new feature value data are added to the disease dictionary data, the classification part 12 re-classifies said data automatically or by the command from the input device and updates the results of reclassification.

Action of the disease diagnosis support system in the abovementioned configuration will be explained below.

Figure 5:
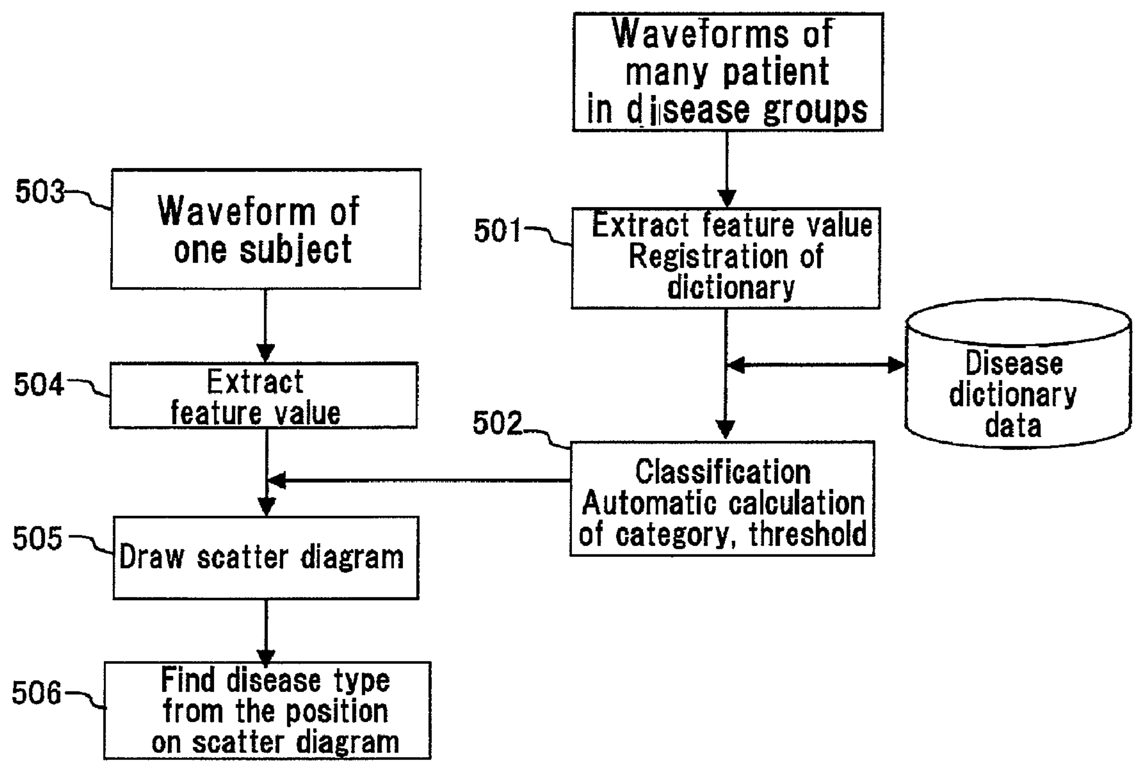

FIG. 5 shows the flow of the action.

The feature value data, consisting of feature values (gradient, integrated value and presence/absence of re-rise) extracted from hemoglobin change waveforms of many groups of patients whose diagnosis has been confirmed, are registered in the dictionary in advance (Step 1). By classifying the disease dictionary data of these many patient groups by automatic clustering, threshold values are automatically calculated (Step 502). This work can be performed at any point after the adequate number of data for statistical processing is obtained.

Then, when the results (hemoglobin change waveform) measured for the subject A by the biological photometric device 40 are input in the analysis part 10 (step 503), the feature values, namely gradient, integrated value and the presence/absence of re-rise are calculated from the hemoglobin change waveforms (Step 504). The display part 30 produces a scatter diagram in which the axis of abscissa represents one of the two feature values of the disease dictionary data registered in the dictionary and the axis of ordinate represents the other, and displays individual data positions attached with the label of disease group on the scatter diagram (Step 505). Lines surrounding the combination of threshold values or the area demarcated by the combination of threshold values calculated by the classification 12 are displayed as superimposed on the scatter diagram.

Figure 6:
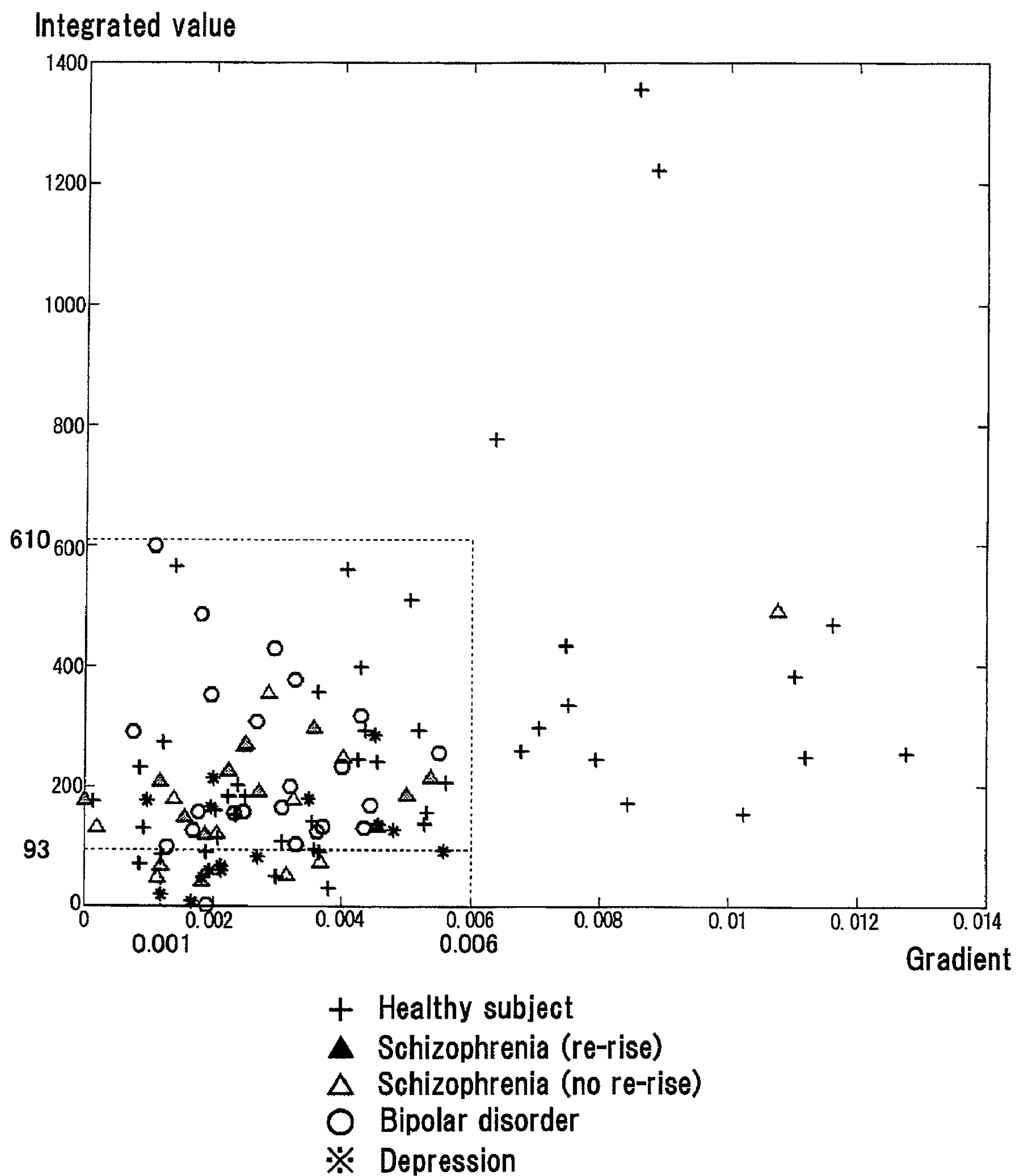

An example of scatter diagram is shown in FIG. 6. In the scatter diagram shown in FIG. 6, the axes of abscissa and ordinate show gradients and integrated values, respectively, and the healthy cases, schizophrenia, bipolar disorder and depression are labeled by "+", "□" or "▲", "○" and "*", respectively. The combination of threshold values is shown by a dotted line. The example shown here shows the results of clustering disease dictionary data groups including 45 healthy cases, 24 schizophrenia cases, 15 depression cases and 23 bipolar disorder cases, and displays the combination of threshold values classified in the following (1), (2), (4) and (5).

(1) The integrated value of 610 or higher or the gradient of 0.006 or higher.

(2) The integrated value of less than 610, the gradient of less than 0.006, and the integrated value of 93 or higher.

(3) The integrated value of less than 610, the gradient of less than 0.006 and the integrated value of less than 93.

(4) The combination of (3) with the gradient of 0.001 or higher.

(5) The combination of (3) with the gradient of less than 0.001.

These combinations of threshold values were selected such that the presence probability of each disease group contained in each type shows the largest possible bias. The presence probability of healthy case group is high in type (1), while the presence probability of schizophrenia and bipolar disorder patients are high in type (4) and type (5), respectively. However, schizophrenia and bipolar disorder groups are mixed in type (2). There is a difference that the hemoglobin change waveform re-rises after the completion of the task in the schizophrenia group as shown in FIG. 4, while it does not re-rise in the bipolar disorder group. Accordingly, in the present embodiment, different colors (□ and ▲) are used to identify whether or not the hemoglobin change waveform re-rises after the completion of the task in the schizophrenia group in order to show the difference from the bipolar disorder group in type (2).

On the other hand, once the feature values similar to the two feature values used for producing the scatter diagram are calculated for the subject A, the position determined based on these feature values is displayed on the scatter diagram with a label of subject A (Step 506). As mentioned above, because the scatter diagram shows the distribution of disease groups and the classification based on the combination of thresholds, by looking the position of the subject A displayed thereon, it is possible to know the type of the subject and identify which disease group the subject is highly likely to belong to. In such case, by adding a clearly identifiable color or mark presenting the third feature to the label of subject A, it is possible to identify whether the schizophrenia group or the bipolar disorder group is more likely even if the two groups are mixed or they are classified as type (2).

Figure 7:
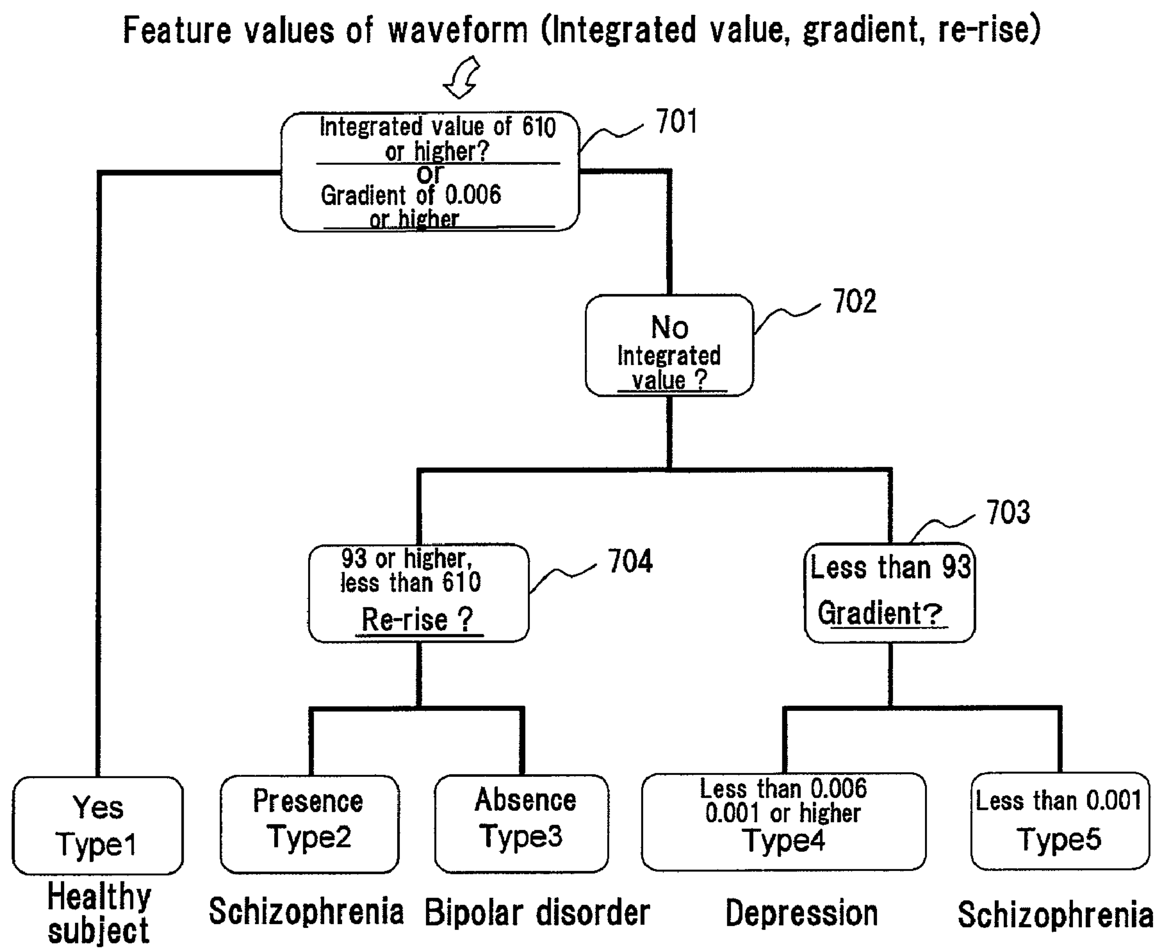

The algorithm which is equivalent to such judgment is shown in FIG. 7. In the disease diagnosis support system of the present embodiment, the plotting of feature values of the subject on a scatter diagram is equivalent to the implementation of judgment flow from step 701 to step 703, and only when it is classified in the type (2), the integrated value of which is 93 or more and less than 610, the judgment is completed only by confirming the presence or absence of re-rise, the third feature value (step 704). With respect of the step 704, as mentioned above, marking of the presence or absence of re-rise in different color in advance is equivalent to the implementation of judgment flow in step 704. In this case, the presence or absence of re-rise was manually selected by using the value 20, which represents the best classification between the type (2) (schizophrenia) and type (3) (bipolar disorder) in the data group requiring judgment of step 704.

Figure 8:
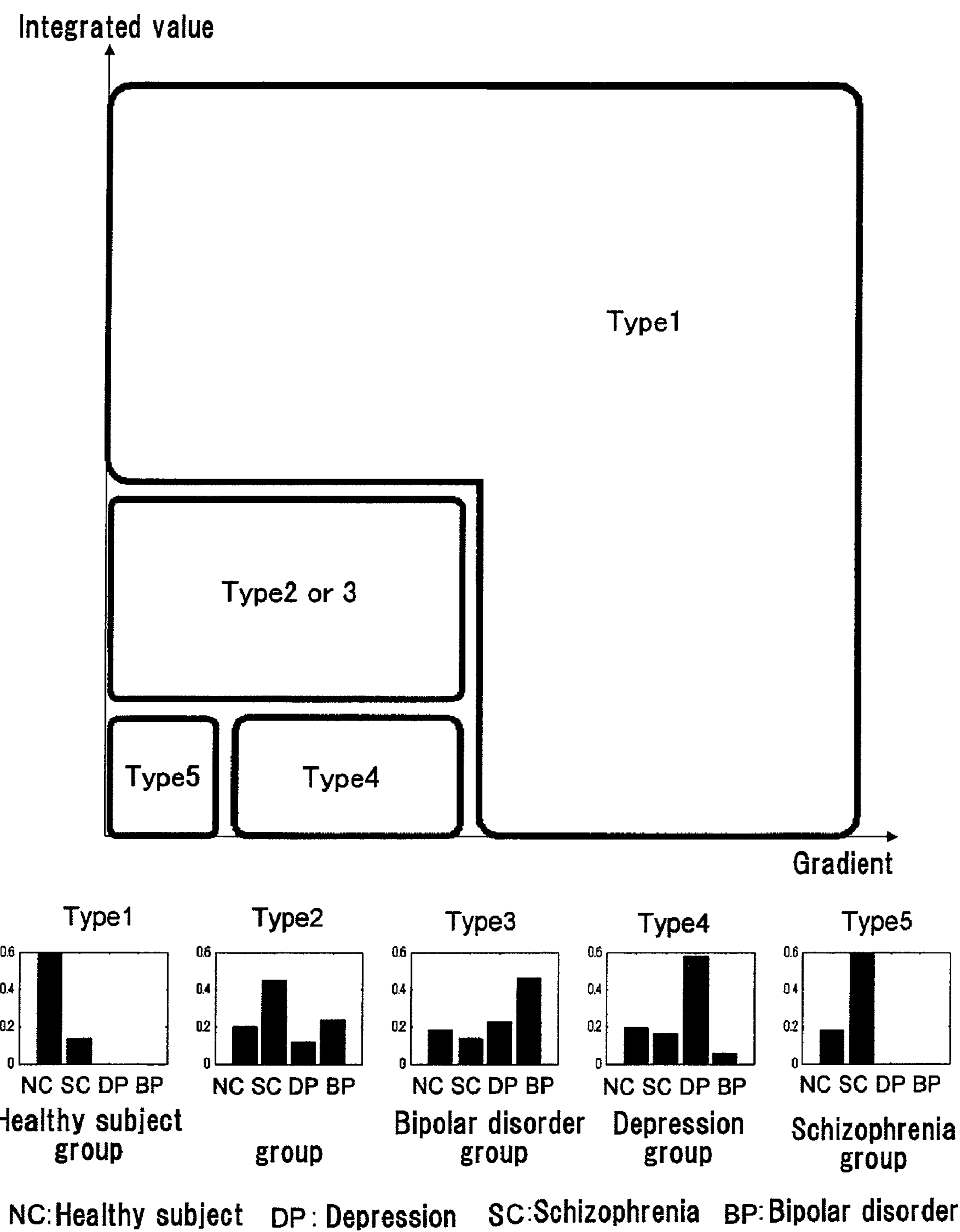

FIG. 6 shows only the scatter diagram, but the number of diseases contained in each type can be shown in a bar chart and others, in addition to the scatter diagram. This may help to identify the accuracy of classification. An example of display is shown in FIG. 8. The examples shown in FIG. 8 displays scatter diagrams similar to FIG. 6 (above) and the bar diagrams for the number of patients (bottom). These diagrams show that the presence probabilities of healthy cases, depression patients and schizophrenia patients account for high percentages in type (1), (4) and (5), respectively. Accordingly, the accuracy of judgment is higher if the subject A belongs to either of these types.

According to the present embodiment, it is possible to recognize at a glance which disease group the subject is classified in, and where the subject is positioned in the whole disease group by superimposing the feature values of the subject on the scatter diagram of the disease registration data registered in advance. This recognition becomes even easier particularly by displaying the surrounding lines (area) demarcating the classified type on the scatter diagram.

The second embodiment will be explained below.

Basic functions of the biological photometric device 40, the analysis part 10, the data storage part 20 and the display part 30 in this second embodiment are same with those in the aforementioned embodiment, but the second embodiment is characterized by the addition of temporal data processing functions which show changes in data measured at different points of time for the same subject.

More specifically, the second embodiment is identical with the first embodiment in that a scatter diagram is produced by using the disease dictionary data stored in the data storage part 20, the disease groups are classified into given types and displayed with the scatter diagram in the display part 30 and the feature values calculated for the subject are displayed superimposed on the scatter diagram. However, once the feature value of hemoglobin change waveform of the subject A measured by the biological photometric device 40 is obtained, the temporal data processing part reads out the feature values of the same subject which have been already extracted, and displays these past feature values with newly obtained feature values. In this case, the data is shown in the way with which temporal change of the data can be known, by using, for example, an arrow indicating the direction from the past to new data. The actions of the temporal data processing part can be performed automatically at the same time with the processing of new data, but it is also possible to send a command to display past data via an input device and to set the number of past data to be displayed.

Figure 9:
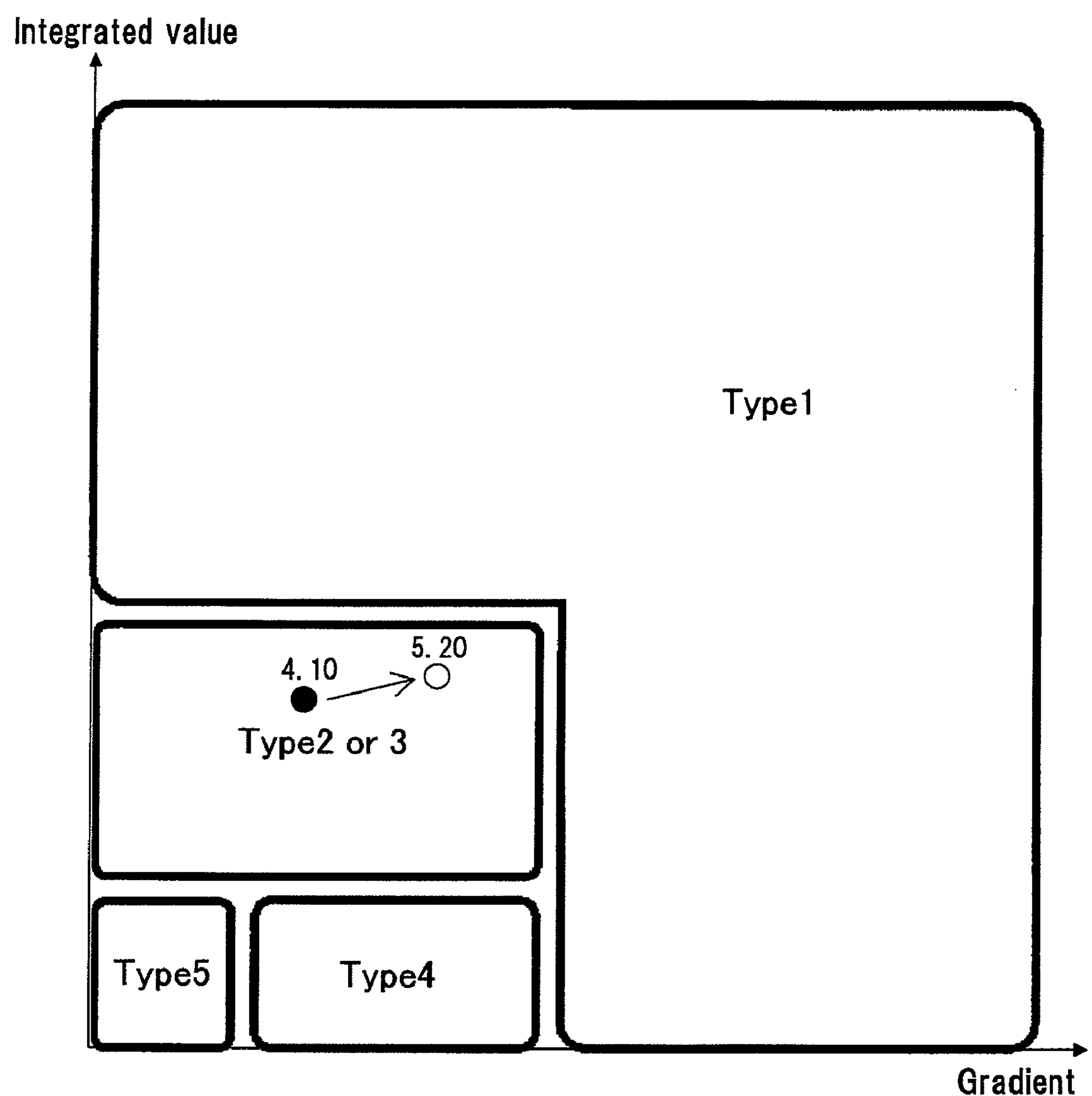
FIG. 9 A diagram showing another examples of a scatter diagram displayed by the disease diagnosis support system of the present invention FIG. 10 A diagram showing an example of display in the third embodiment of the present invention.

FIG. 9 shows an example of display. In the shown example past two data and newly measured data are displayed in sequence indicated by the arrow. Display of temporal changes may help understanding improvements or aggravation of the conditions of patients, and make them be used in confirming therapy effects and producing a treatment policy including medication.

This embodiment enables the observation of not only the data at one point of the subject but also temporal changes, and provides an extremely useful system applicable not only to the assessment of psychiatric disorders but also to the treatment.

The third embodiment will be explained below.

This embodiment differs from the abovementioned embodiment in the point that the third embodiment produces a one-dimensional scatter diagram. In the present embodiment, based on the hemoglobin change waveform measured by the biological photometric device 40, gradient or integrated value is obtained, for example. And as shown in FIG. 10, depending on thus obtained value, it is displayed with label on individual data position on the one-dimensional scatter diagram on the display.

Figure 10:
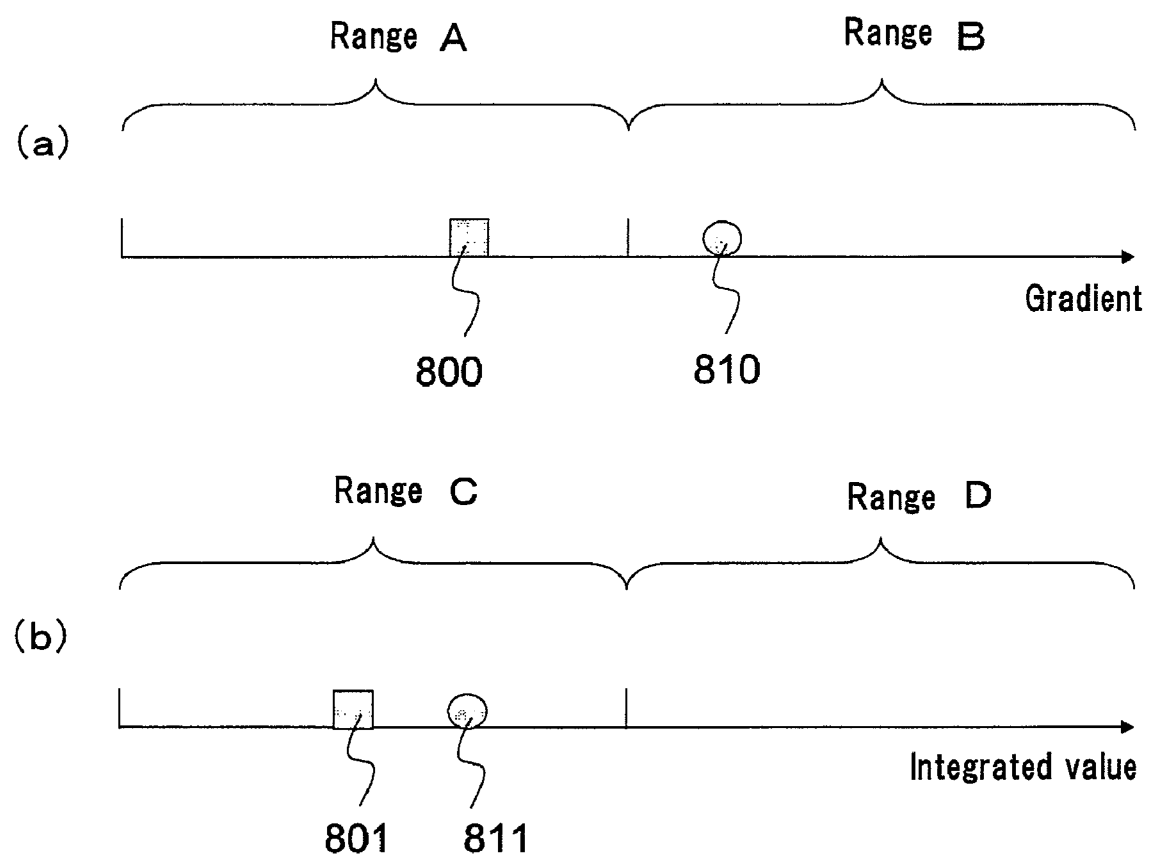

For the gradient values shown in FIG. 10(*a*), the border between range A and range B is the border between type 1 and type 4 in FIG. 9. Therefore, the range A and range B are defined as the range for those with suspected disease and the range of healthy cases, respectively. For example, when the gradient value is within the range B as the feature value 810, the subject is a healthy case, and the feature value 810 is displayed as the range of healthy cases. When the gradient value is within the range A, as in the feature value 800, the subject is suspected to have disease, and the feature value 800 is displayed on the one-dimensional scatter diagram.

Similarly, for the integrated values in FIG. 10(*b*), the border between the range C and the range D is the border between the type 1 and the type 2 or 3. Accordingly, the range C and the range D are defined as the range of those with suspected disease and the range of healthy cases, respectively. When the gradient value is within the C range, as the feature values 801 and 811, the subject is suspected to have disease and each value is displayed on the one-dimensional scatter diagram.

Further, psychiatric disorder may be determined and displayed by using two one-dimensional scatter diagrams. If either gradient value or integrated value exceeds a threshold value, the subject is displayed as a healthy case. For example, in case the feature values 810 and 811 are the values for the same subject, since the feature value 810 is in the range B, the subject is judged as healthy and this judgment result is displayed. Also, in case the feature values 800 and 801 are the values for the same subject, since none of them exceeds the threshold values, the subject is judged as having disease and this judgment result is displayed.

As mentioned above, disease conditions can be judged based on the range in which the feature value is positioned on the one-dimensional scatter diagram.

The embodiments mentioned above are explained with the example of psychiatric disorders, but the disease diagnosis support system may be applied to other diseases than psychiatric disorders as far as any correlation with the optical bio-measurement signals is observed.

The invention claimed is:

1. A disease diagnosis support apparatus, comprising an analysis part which extracts plural kinds of feature values from hemoglobin signals measured by optical bio-measurement, a classification part which classifies the feature amount data into plural types using a combination of threshold values of the feature amounts and a display part which displays the results of analysis performed by the analysis part, wherein the display part produces a scatter diagram for an integrate value and a gradient of a specific part of the hemoglobin signal waveform among the plural kinds of feature values, displays the integrate value and the gradient plotted on the scatter diagram and displays surrounding lines demarcating types classified by the classification part on the scatter diagram;

wherein at least the analysis part, the classification part and the display part are effected, at least in part, by a hardware processor.

2. A disease diagnosis support system according to claim 1, comprising a data storage part which stores the feature values of optical bio-measurement data for many objects including the objects of multiple disease groups, wherein the display part displays the analysis results obtained by the analysis part in association with the dictionary data.

3. The disease diagnosis support system according to claim 1, wherein the display part produces a scatter diagram, on which one of the two kinds of feature values among the plural feature values in the dictionary data is plotted on the axis of abscissa, and the other on the axis of ordinate, and two kinds of the feature values extracted for the subject to be assessed are displayed superimposed on the scatter diagram.

4. The disease diagnosis support system according to claim 2, comprising a classification part which classifies data contained in the dictionary data stored in the storage part into multiple different types, wherein the display part displays the types classified by the classification part superimposed on the scatter diagram.

5. The disease diagnosis support system according to claim 4, wherein the classification part classifies the data in the dictionary data according to the combination of threshold values of plural kinds, in which the classification is performed by using the combination of threshold values that may minimize the entropy of disease group distribution in the classified types.

6. The disease diagnosis support system according to claim 4, wherein the display part displays the number of disease groups contained in each type classified by the classification part together with the scatter diagram.

7. The disease diagnosis support system according to claim 3, wherein the display part updates the results of classification, according to the update of data stored in the storage part, and displays the results of classification on the display part.

8. The disease diagnosis support system according to claim 1, wherein the analysis part is equipped with a memory part which stores analysis results of the data measured for the same subject at different times and displays the temporal changes in the analysis results in the display part.

9. The disease diagnosis support system according to claim 1, wherein the disease group contains schizophrenia, bipolar disorders and depression.

10. The disease diagnosis support system according to claim 1, wherein the plural kinds of feature values include integrated values and gradients for a specific part of the optical bio-measurement waveforms.

11. A diagnosis support method for proving information necessary for diagnosing disease of the subject by using hemoglobin signals measured by optical bio-measurement, which uses an optical bio-measurement apparatus comprising an analysis mart, a bio-measurement part and a display part and comprises the steps of;

extracting by using the analysis part one or more feature values from each hemoglobin signal of the object whose diagnosis has been established and produces dictionary data, and extracting one or more feature values from hemoglobin signals of a subject to be examined, classifying by using the classification part the feature amount data into plural types using a combination of threshold values of the feature amounts;

producing by using the display part a scatter diagram for an integrate value and a gradient of a specific part of the hemoglobin signal waveform among the plural kinds of feature values, and displaying the integrate value and the gradient plotted on the scatter diagram and surrounding lines demarcating types classified by the classification part on the scatter diagram;

displaying the results of analysis performed by the analysis part, wherein at least the anal sis part, the classification part and the display part are effected, at least in part, by a hardware processor.

12. The diagnosis support method according to claim 11, which contains a step of classifying one or more feature values extracted from each hemoglobin signal of the object whose diagnosis has been established into multiple types, wherein the multiple types classified at the classification step are displayed together with the scatter diagram in the displaying step.

13. The diagnosis support method according to claim 11, wherein the step of producing the dictionary data contains a step of updating the dictionary data, and the classification step contains a step of updating the classification after updating of dictionary data.

14. The diagnosis support method according to claim 11, which contains a step of storing analysis data of the data measured for the same subject at different times, wherein temporal changes of the analysis results is displayed on the scatter diagram in the displaying step.

15. The diagnosis support method according to claim 11, which contains a step of measuring hemoglobin signals by optical bio-measurement, wherein the hemoglobin signals are those measured while a task is given intermittently to the subject to be examined and indicating hemoglobin changes before and after the task.

* * * * *